United States Patent
Levinson et al.

(10) Patent No.: US 11,986,421 B2
(45) Date of Patent: May 21, 2024

(54) COOLING DEVICES WITH FLEXIBLE SENSORS

(71) Applicant: Zeltiq Aesthetics, Inc., Pleasanton, CA (US)

(72) Inventors: Mitchell Levinson, Pleasanton, CA (US); Jesse N. Rosen, Albany, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 920 days.

(21) Appl. No.: 16/824,530

(22) Filed: Mar. 19, 2020

(65) Prior Publication Data

US 2020/0214883 A1   Jul. 9, 2020

Related U.S. Application Data

(63) Continuation of application No. 11/528,189, filed on Sep. 26, 2006, now abandoned.

(51) Int. Cl.
*A61F 7/00* (2006.01)
*A61B 5/00* (2006.01)
(Continued)

(52) U.S. Cl.
CPC ............... *A61F 7/10* (2013.01); *A61B 5/411* (2013.01); *A61B 5/6843* (2013.01);
(Continued)

(58) Field of Classification Search
CPC ............... A61F 7/00; A61F 2007/0052; A61F 2007/0063; A61F 2007/0075;
(Continued)

(56) References Cited

U.S. PATENT DOCUMENTS

| 681,806 A | 9/1901 | Mignault |
|---|---|---|
| 889,810 A | 6/1908 | Robinson |

(Continued)

FOREIGN PATENT DOCUMENTS

| AU | 2011253768 A1 | 6/2012 |
|---|---|---|
| CA | 2441489 A1 | 3/2005 |

(Continued)

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

(Continued)

*Primary Examiner* — Ahmed M Farah
(74) *Attorney, Agent, or Firm* — Mintz, Levin, Cohn, Ferris, Glovsky and Popeo, P.C.

(57) ABSTRACT

A device for exchanging heat with a subject having skin is provided. The device includes a heat exchanging member having a heat transfer surface configured to form a heat conducting interface with the subject's skin. The device further includes a substantially flexible sensing device disposed in the interface between the heat exchanging member and the subject's skin. The sensing device is configured to measure a parameter of the interface without substantially impeding heat transfer between the heat exchanging member and the subject's skin.

5 Claims, 5 Drawing Sheets

(51) Int. Cl.

| | | |
|---|---|---|
| *A61F 7/10* | (2006.01) | |
| *G05D 23/19* | (2006.01) | |
| *G05D 23/22* | (2006.01) | |
| *G05D 23/24* | (2006.01) | |
| *A61B 17/00* | (2006.01) | |
| *A61B 18/00* | (2006.01) | |
| *A61B 90/00* | (2016.01) | |
| *A61F 7/02* | (2006.01) | |

(52) U.S. Cl.
CPC ......... *G05D 23/1919* (2013.01); *G05D 23/22* (2013.01); *G05D 23/24* (2013.01); *A61B 2017/00088* (2013.01); *A61B 2017/00092* (2013.01); *A61B 2017/00101* (2013.01); *A61B 2018/00011* (2013.01); *A61B 2018/00023* (2013.01); *A61B 2018/00047* (2013.01); *A61B 2018/00744* (2013.01); *A61B 2018/00791* (2013.01); *A61B 2090/064* (2016.02); *A61B 2562/164* (2013.01); *A61F 2007/0001* (2013.01); *A61F 2007/0075* (2013.01); *A61F 2007/0228* (2013.01); *A61F 2007/029* (2013.01)

(58) Field of Classification Search
CPC ... A61F 2007/0228; A61F 2007/00231; A61B 5/6843; A61B 5/6867; A61B 5/6879; A61B 5/6885; A61B 2562/164; A61B 2562/22; G05D 23/22; G05D 23/24; G05D 23/27535; G05D 23/30
USPC ............... 607/96, 108, 112; 606/20–24
See application file for complete search history.

(56) References Cited

U.S. PATENT DOCUMENTS

| | | |
|---|---|---|
| 2,516,491 A | 7/1950 | Swastek |
| 2,521,780 A | 9/1950 | Dodd et al. |
| 2,726,658 A | 12/1955 | Chessey |
| 2,766,619 A | 10/1956 | Myron et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | Eidus et al. |
| 3,282,267 A | 11/1966 | William |
| 3,341,230 A | 9/1967 | Louis |
| 3,502,080 A | 3/1970 | Hirschhorn |
| 3,566,871 A | 3/1971 | Richter et al. |
| 3,587,577 A | 6/1971 | Smirnov et al. |
| 3,591,645 A | 7/1971 | Selwitz |
| 3,692,338 A | 9/1972 | Didier |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,008,910 A | 2/1977 | Roche |
| 4,026,299 A | 5/1977 | Sauder |
| 4,140,130 A | 2/1979 | Storm, III |
| 4,149,529 A | 4/1979 | Copeland et al. |
| 4,178,429 A | 12/1979 | Scheffer |
| 4,202,336 A | 5/1980 | van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdoerffer et al. |
| 5,018,521 A | 5/1991 | Campbell |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed et al. |
| 5,143,063 A | 9/1992 | Fellner |
| 5,148,804 A | 9/1992 | Hill et al. |
| 5,158,070 A | 10/1992 | Dory |
| 5,160,312 A | 11/1992 | Voelkel |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,327,886 A | 7/1994 | Chiu |
| 5,330,745 A | 7/1994 | Mcdow |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan |
| 5,433,717 A | 7/1995 | Rubinsky et al. |
| 5,456,703 A | 10/1995 | Beeuwkes, III |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens |
| 5,603,221 A | 2/1997 | Maytal |

(56) References Cited

U.S. PATENT DOCUMENTS

| | | |
|---|---|---|
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,665,053 A | 9/1997 | Jacobs |
| 5,672,172 A | 9/1997 | Zupkas |
| 5,700,284 A | 12/1997 | Owens |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton |
| 5,755,755 A | 5/1998 | Panyard |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A | 9/1998 | Strauss |
| 5,814,040 A | 9/1998 | Nelson et al. |
| 5,817,050 A | 10/1998 | Klein |
| 5,817,149 A | 10/1998 | Owens |
| 5,817,150 A | 10/1998 | Owens |
| 5,830,208 A | 11/1998 | Muller |
| 5,833,685 A | 11/1998 | Tortal et al. |
| 5,844,013 A | 12/1998 | Kenndoff et al. |
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,954,680 A | 9/1999 | Augustine |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | Mcclure et al. |
| 6,049,927 A | 4/2000 | Thomas et al. |
| 6,051,159 A | 4/2000 | Hao |
| 6,071,239 A | 6/2000 | Cribbs et al. |
| 6,074,415 A | 6/2000 | Der |
| 6,093,230 A | 7/2000 | Johnson, III et al. |
| 6,102,885 A | 8/2000 | Bass |
| 6,104,952 A | 8/2000 | Tu et al. |
| 6,104,959 A | 8/2000 | Spertell |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg, et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chomenky et al. |

(56) References Cited

U.S. PATENT DOCUMENTS

| | | |
|---|---|---|
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat et al. |
| 6,749,624 B2 | 6/2004 | Knowlton |
| 6,753,182 B1 | 6/2004 | Kadkade et al. |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | Mchale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | O'connor et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 9,149,322 B2 | 10/2015 | Knowlton |
| 9,375,345 B2 * | 6/2016 | Levinson ............. A61F 7/0085 |
| 9,408,745 B2 | 8/2016 | Levinson et al. |
| 10,675,178 B2 | 6/2020 | Levinson et al. |
| 2001/0005791 A1 | 6/2001 | Ginsburg et al. |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0109912 A1 | 6/2003 | Joye et al. |
| 2003/0114885 A1 | 6/2003 | Nova et al. |
| 2003/0120268 A1 | 6/2003 | Bertolero et al. |
| 2003/0125649 A1 | 7/2003 | Mcintosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |

(56) References Cited

U.S. PATENT DOCUMENTS

| | | |
|---|---|---|
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Rave et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0049526 A1 | 3/2005 | Baer |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0122509 A1 | 6/2006 | Desilets |
| 2006/0189964 A1 | 8/2006 | Anderson et al. |
| 2006/0200063 A1 | 9/2006 | Munro et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | Delonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0193278 A1* | 8/2007 | Polacek .............. F25B 21/02 62/3.2 |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Einav et al. |
| 2009/0312693 A1 | 12/2009 | Thapliyal et al. |
| 2009/0326621 A1 | 12/2009 | El-galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0198064 A1 | 8/2010 | Perl et al. |
| 2010/0241023 A1 | 9/2010 | Gilbert |
| 2010/0268220 A1 | 10/2010 | Johnson et al. |
| 2010/0280582 A1 | 11/2010 | Baker et al. |

(56) References Cited

U.S. PATENT DOCUMENTS

| | | |
|---|---|---|
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Michael |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Winozil et al. |
| 2011/0238050 A1 | 9/2011 | Allison et al. |
| 2011/0238051 A1 | 9/2011 | Levinson et al. |
| 2011/0257642 A1 | 10/2011 | Griggs, III et al. |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0041525 A1 | 2/2012 | Karni |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1* | 1/2013 | Altshuler ............ A61B 18/203 600/306 |
| 2013/0019374 A1 | 1/2013 | Schwartz |
| 2013/0035680 A1 | 2/2013 | Ben-haim et al. |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0303904 A1 | 11/2013 | Barthe et al. |
| 2013/0303905 A1 | 11/2013 | Barthe et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0277219 A1 | 9/2014 | Nanda |
| 2014/0277303 A1 | 9/2014 | Biser et al. |
| 2014/0303697 A1 | 10/2014 | Anderson et al. |
| 2015/0216719 A1 | 8/2015 | Debenedictis et al. |
| 2015/0216720 A1 | 8/2015 | Debenedictis et al. |
| 2015/0216816 A1 | 8/2015 | Oneil et al. |
| 2015/0223975 A1 | 8/2015 | Anderson et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |
| 2019/0125424 A1 | 5/2019 | DeBenedictis et al. |
| 2019/0142493 A1 | 5/2019 | Debenedictis et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 | 11/1983 |
| JP | S6094113 U | 6/1985 |
| JP | 62082977 A | 4/1987 |
| JP | 63076895 A | 4/1988 |
| JP | 01223961 A | 9/1989 |

(56) References Cited

FOREIGN PATENT DOCUMENTS

| | | |
|---|---|---|
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 3065657 U | 4/1999 |
| JP | 2000503154 A | 3/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 3655820 B2 | 3/2005 |
| JP | 2005065984 A | 3/2005 |
| JP | 2005110755 A | 4/2005 |
| JP | 2005509977 A | 4/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 3/2000 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9300807 A1 | 1/1993 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

(56) References Cited

OTHER PUBLICATIONS

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.
Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.
Donski, P. K. et al., "The Effects of Cooling no Experimental Free Flap Survival," British Journal of Plastic Surgery, vol. 33, 1980, pp. 353-360.
Duck, F. A., Physical Properties of Tissue, Academic Press Ltd., chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties Of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002, pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry, 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: The Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.

(56) References Cited

OTHER PUBLICATIONS

Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.

Nurnberger, F. "So-Called Cellulite: An Invented Disease," Journal of Dermatologic Surgery and Oncology, Mar. 1978, pp. 221-229.

Pease, G. R. et al., "An Integrated Probe for Magnetic Resonance Imaging Monitored Skin Cryosurgery," Journal of Biomedical Engineering, vol. 117, Feb. 1995, pp. 59-63.

Pech, P. et al., "Attenuation Values, Volume Changes and Artifacts in Tissue Due to Freezing," Acta Radiologica, vol. 28, Issue 6, 1987, pp. 779-782.

Peterson, L. J. et al., "Bilateral Fat Necrosis of the Scrotum," Journal of Urology, vol. 116, 1976, pp. 825-826.

Phinney, S. D. et al., "Human Subcutaneous Adipose Tissue Shows Site-Specific Differences in Fatty Acid Composition," The American Journal of Clinical Nutrition, vol. 60, 1994, pp. 725-729.

Pierard, G.E. et al., "Cellulite: From Standing Fat Herniation to Hypodermal Stretch Marks," The American Journal of Dermatology, vol. 22, Issue 1, 2000, pp. 34-37, [Abstract].

Pope, K. et al. "Selective Fibrous Septae Heating: An Additional Mechanism of Action for Capacitively Coupled Monopolar Radiofrequency" Thermage, Inc. Article, Feb. 2005, 6pgs.

Quinn, P. J. "A Lipid-Phase Separation Model of Low-Temperature Damage to Biological Membranes," Cryobiology, 22, 1985, 128-146.

Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.

Renold, A.E. et al. "Adipose Tissue" in Handbook of Physiology, Chapter 15, (Washington, D.C., 1965) pp. 169-176.

Rossi, A. B. R. et al. "Cellulite: a Review," European Academy of Dermatology and Venercology, 2000, pp. 251-262, 12 pgs.

Rubinsky, B. "Principles of Low Temperature Cell Preservation," Heart Failure Reviews, vol. 8, 2003, pp. 277-284.

Rubinsky, B. et al., "Cryosurgery: Advances in the Application of low Temperatures to Medicine," International Journal of Refrigeration, vol. 14, Jul. 1991, pp. 190-199.

Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.

Schoning, P. et al., "Experimental Frostbite: Freezing Times, Rewarming Times, and Lowest Temperatures of Pig Skin Exposed to Chilled Air," Cryobiology 27, 1990, pp. 189-193.

Shephard, R. J. "Adaptation to Exercise in the Cold," Sports Medicine, vol. 2, 1985, pp. 59-71.

Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.

Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.

Thermage, News Release, "Study Published in Facial Plastic Surgery Journal Finds Selective Heating of Fibrous Septae Key to Success and Safety of Thermage ThermaCool System," Jun. 20, 2005, 2 pages.

"ThermaCool Monopolar Capacitive Radiofrequency, The one choice for nonablative tissue tightening and contouring", Thermage, Inc. Tech Brochure, Nov. 30, 2005, 8 pgs.

Vallerand et al. "Cold Stress Increases Lipolysis, FFA Ra and TG/FFA Cycling in Humans," Aviation, Space, and Environmental Medicine 70(1), 1999, pp. 42-50.

Wang, X. et al., "Cryopreservation of Cell/Hydrogel Constructs Based on a new Cell- Assembling Technique," Sep. 5, 2009, 40 pages.

Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.

Winkler, C. et al., "Gene Transfer in Laboratory Fish: Model Organisms for the Analysis of Gene Function," in Transgenic Animals, Generation and Use (The Netherlands 1997), pp. 387-395.

Young, H. E. et al. "Isolation of Embryonic Chick Myosatellite and Pluripotent Stem Cells" The Journal of Tissue Culture Methods, vol. 14, Issue 2, 1992, pp. 85-92.

Zelickson, B. et al., "Cryolipolysis for Noninvasive Fat Cell Destruction: Initial Results from a Pig Model", 35 Dermatol. Sug., 2009, pp. 1-9.

Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

COOLING DEVICES WITH FLEXIBLE SENSORS

CROSS REFERENCE TO RELATED APPLICATION

The present application is a continuation of U.S. patent application Ser. No. 11/528,189, filed Sep. 6, 2006, now pending, which is incorporated herein by reference in its entirety.

TECHNICAL FIELD

The present application relates to cooling devices, systems, and methods for exchanging heat with subcutaneous lipid-rich cells of a subject.

BACKGROUND

As statistics have shown, excess body fat increases the likelihood of developing various diseases and can detract from personal appearance and athletic performance. One conventional technique of controlling excess body fat is liposuction that can selectively remove body fat to sculpt a person's body. One drawback of liposuction is that it is a complex surgical procedure that can have serious and occasionally even fatal complications.

Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction.

Other non-invasive treatment methods include applying heat to a zone of subcutaneous lipid-rich cells. U.S. Pat. No. 5,948,011 discloses altering subcutaneous body fat and/or collagen by heating the subcutaneous fat layer with radiant energy while cooling the surface of the skin. Another promising method of reducing subcutaneous fat cells is to cool the target cells as disclosed in U.S. Patent Publication No. 2003/0220674, the entire disclosure of which is incorporated herein. U.S. Patent Publication No. 2003/0220674 also discloses methods for selective removal of lipid-rich cells, and avoidance of damage to other structures including dermal and epidermal cells.

In any of these non-invasive treatment methods, temperatures at heat transfer interfaces (e.g., between a treatment device and a skin surface) are important for safety reasons. High interface temperatures may cause scorching of the skin surface, and low interface temperatures may cause frostbite. Therefore, effective devices and methods for accurately measuring the interface temperatures would be desirable.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

A. Overview

The present disclosure describes devices, systems, and methods for exchanging heat with subcutaneous lipid-rich cells. The term "subcutaneous tissue" means tissue lying underneath the dermis and includes adipocytes (fat cells) and subcutaneous fat. It will be appreciated that several of the details set forth below are provided to describe the following embodiments in a manner sufficient to enable a person skilled in the relevant art to make and use the disclosed embodiments. Several of the details and advantages described below, however, may not be necessary to practice certain embodiments of the invention. Additionally, the invention can include other embodiments that are within the scope of the claims but are not described in detail with respect to FIGS. 1-7.

Reference throughout this specification to "one embodiment" or "an embodiment" means that a particular feature, structure, or characteristic described in connection with the embodiment is included in at least one embodiment of the present invention. Thus, the occurrences of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the claimed invention.

One aspect is directed toward a cooling device for removing heat from subcutaneous lipid-rich cells of a subject's skin. The cooling device can include a heat exchanging member having a heat transfer surface configured to form a heat conducting interface with the subject's skin to remove heat from the lipid-rich cells such that the lipid-rich cells are affected while non-lipid-rich cells in the epidermis are not affected. The cooling device can further include a substantially flexible sensing device disposed in the interface between the heat exchanging member and the subject's skin, wherein the sensing device is configured to sense a parameter at the interface without substantially impeding heat transfer between the heat exchanging member and the subject's skin.

Another aspect is directed toward a sensing device for measuring parameters of a heat transfer interface between a subject having skin and a cooling device having a substantially flexible substrate positioned in the heat transfer interface between the subject's skin and the cooling device. The substrate can include a temperature sensor disposed on the surface of the substrate. According to aspects, the temperature sensor is configured to measure a temperature of the heat transfer interface without substantially impeding heat transfer between the cooling device and the subject's skin.

Another aspect is directed toward a method of applying a cooling device configured for removing heat from a subject having skin, the method including disposing a sensing device proximate to the cooling device, the sensing device being substantially flexible and at least partially conforming to the cooling device. The method can further include positioning the cooling device and the sensing device proximate to the subject's skin, wherein the cooling device and the subject's skin form a heat transfer interface, in which the sensing device is positioned. The method can further include measuring a parameter of the heat transfer interface using the sensing device and removing heat from a region of the subject's skin under the epidermis such that lipid-rich cells are affected while non-lipid-rich cells in the epidermis are not affected.

B. System for Selectively Reducing Lipid-Rich Cells

Figure 1:
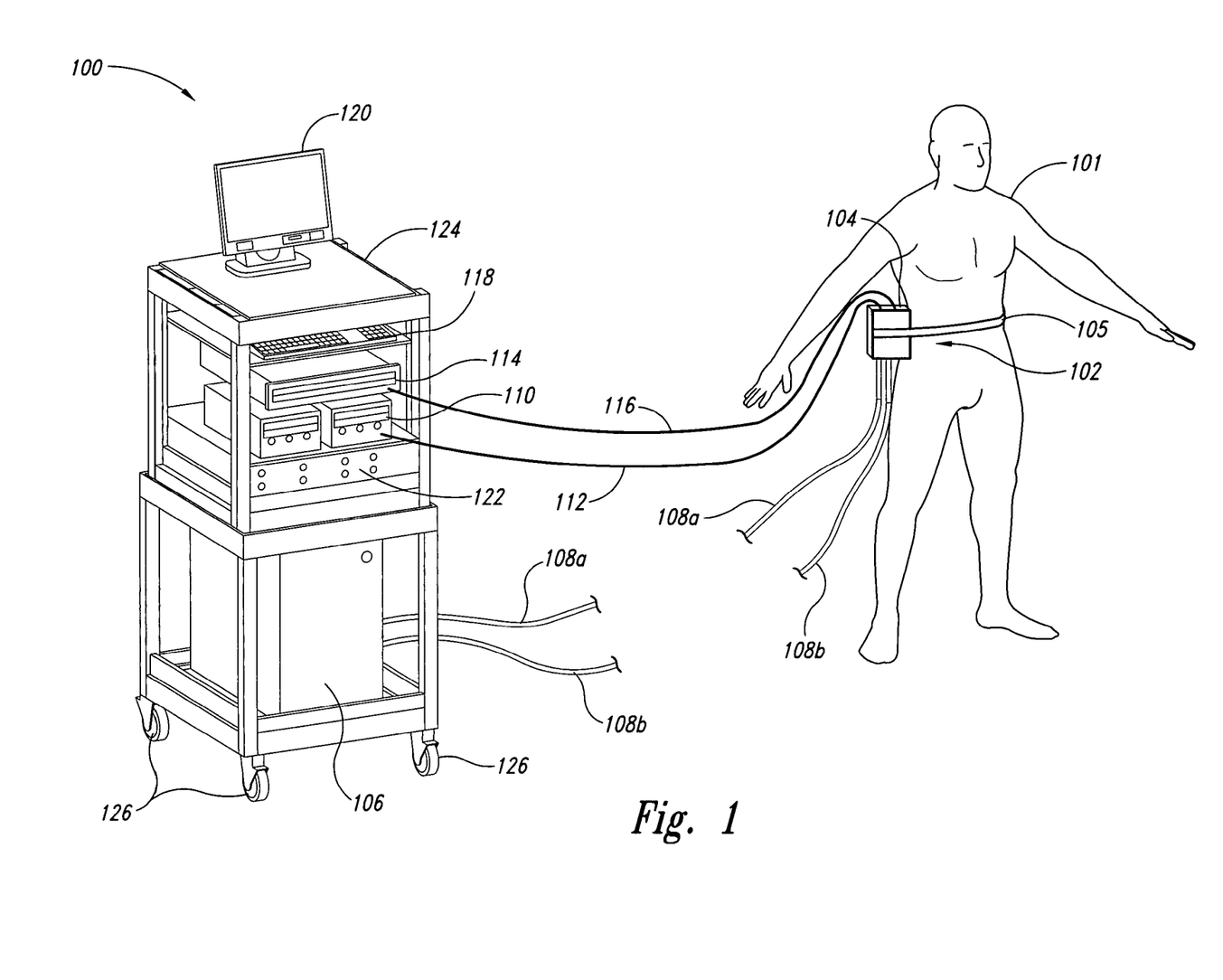
FIG. 1 is an isometric view of a system for exchanging heat with a subject in accordance with an embodiment of the invention.

FIG. 1 is an isometric view of a system 100 for exchanging heat from subcutaneous lipid-rich cells of a subject 101 in accordance with an embodiment of the invention. The system 100 can include a cooling device 104 placed at an abdominal area 102 of the subject 101 or another suitable area for exchanging heat from the subcutaneous lipid-rich cells of the subject 101. The cooling device 104 can be fastened to the subject 101 using, for example, a mechanical fastener (e.g., a belt 105), an adhesive (e.g., an epoxy), suction (e.g., a vacuum or reduced pressure) or any other mechanisms. The cooling device 104 can be configured to heat and/or cool the subject 101. Various embodiments of the cooling device 104 are described in more detail below with reference to FIGS. 2-7.

In one embodiment, the cooling device 104 is configured to cool subcutaneous lipid-rich cells of the subject 101. In such cases, the system 100 can further include a cooling unit 106 and fluid lines 108a-b connecting the cooling device 104 to the cooling unit 106. The cooling unit 106 can remove heat from a coolant to a heat sink and provide the chilled coolant to the cooling device 104 via the fluid lines 108a-b. Examples of the circulating coolant include water, glycol, synthetic heat transfer fluid, oil, a refrigerant, and any other suitable heat conducting fluids. The fluid lines 108a-b can be hoses or other conduits constructed from polyethylene, polyvinyl chloride, polyurethane, and other materials that can accommodate the particular circulating coolant. The cooling unit 106 can be a refrigeration unit, a cooling tower, a thermoelectric chiller, or any other device capable of removing heat from a coolant or municipal water supply.

The cooling device 104 can also include one or more thermoelectric elements, such as Peltier-type thermoelectric elements. In such cases, the system 100 can further include a power supply 110 and a processing unit 114 operatively coupled to the cooling device 104 via electrical cables 112, 116. In one embodiment, the power supply 110 can provide a direct current voltage to the cooling device 104 to effectuate a heat removal rate from the subject 101. The processing unit 114 can monitor process parameters via sensors (not shown in FIG. 1) placed proximate to the cooling device 104 and adjust the heat removal rate based on the process parameters. The processing unit 114 can include an y processor, Programmable Logic Controller, Distributed Control System, and the like.

The processing unit 114 can be in electrical communication with an input device 118, an output device 120, and/or a control panel 122. The input device 118 can include a keyboard, a mouse, a touch screen, a push button, a switch, a potentiometer, and any other device suitable for accepting user input. The output device 120 can include a display screen, a printer, a medium reader, an audio device, and any other device suitable for providing user feedback. The control panel 122 can include indicator lights, numerical displays, and audio devices. In the embodiment shown in FIG. 1, the processing unit 114, power supply 110, control panel 122, cooling unit 106, input device 118, and output device 120 are carried by a rack 124 with wheels 126 for portability. In another embodiment, the various components can be fixedly installed at a treatment site.

One expected advantage of the system 100 is that the cooling device 104 can be applied to the subject 101 irrespective of the current physical condition of the subject 101. For example, the system 100 can be applied even when the subject 101 is not ambulatory or is ill. Another expected advantage is that the system 100 can remove or affect fat non-invasively without piercing the skin of the subject 101. Yet another expected advantage is that the system 100 is compact and can be used in an outpatient facility or a doctor's office. A further expected advantage is that the system 100 can quickly cool lipid-rich cells in a subcutaneous layer without requiring high-voltage power supplies.

C. Cooling Devices With Flexible Sensors

Figure 2:
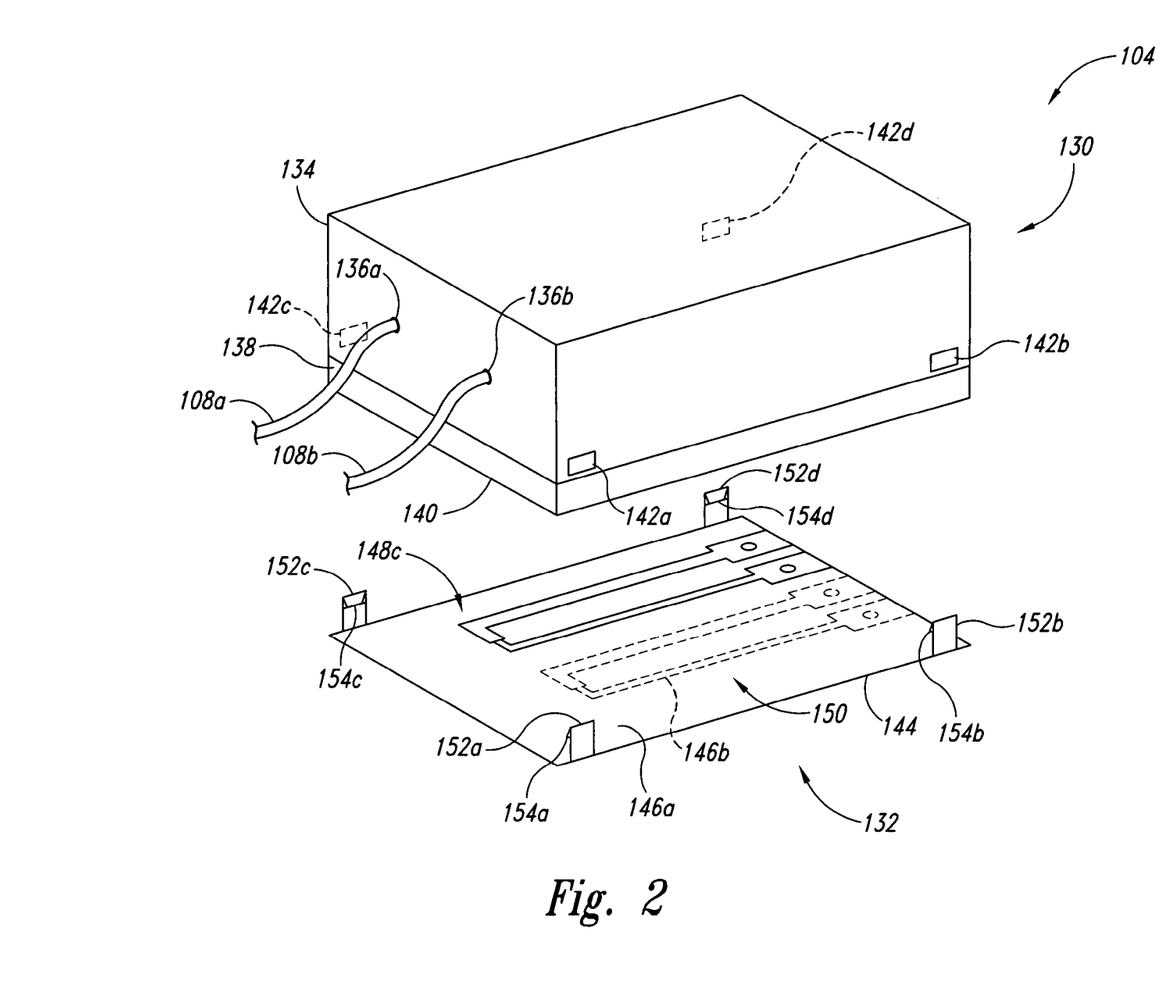
FIG. 2 is a partially exploded isometric view of a cooling device with flexible sensors in accordance with an embodiment of the invention.

FIG. 2 is a partially exploded isometric view of a cooling device 104 in accordance with one embodiment of the invention and suitable for use in the system 100. In this example, the cooling device 104 includes a heat exchanging member 130 and a sensing device 132 affixed to the heat exchanging member 130. The cooling device 104 is generally configured for manual positioning, and/or it can be strapped or otherwise configured to be releasably attached to the subject 101. The sensing device 132 is configured to measure a parameter at an interface of the cooling device 104 and the skin of the subject 101.

The heat exchanging member 130 can include a housing 134 and fluid ports 136a-b coupled to the fluid lines 108a-b. In one example, the housing 134 is generally rectangular, but in other examples, the housing 134 can be cubic, spherical, semi-spherical, or any other desired shape. The housing 134 can include features for attaching the sensing device 132. In the illustrated example, the housing 134 includes a plurality of indentations 142 (identified individually as 142a-d). In other examples, the housing 134 can include threaded apertures, channels, slots, pegs, or any other suitable attachment mechanism. The housing 134 can be constructed from polymeric materials, metals, ceramics, woods, and/or other suitable materials.

The heat exchanging member 130 can further include an interface member 138 at least partially in the housing 134. The interface member 138 has a heat exchanging surface 140 for transferring heat to/from the subject 101. In one example, the heat exchanging surface 140 is generally planar, but in other examples, the heat exchanging surface 140 can be non-planar (e.g., curved, faceted, etc.) The interface member 138 can be constructed from any suitable material with a thermal conductivity greater than 0.05 Watts/Meter Kelvin, and in many examples, the thermal conductivity is more than 0.1 Watts/Meter Kelvin. Examples of suitable materials include aluminum, copper, other metals, metal alloys, graphite, ceramics, some polymeric materials, composites, or fluids contained in a flexible membrane. In other embodiments, portions of the heat exchanging surface 140 can be constructed from an insulating material with a thermal conductivity less than 0.05 Watts/Meter Kelvin.

The sensing device 132 can include a substrate 144 having a first surface 146a and a second surface 146b. The substrate 144 can have a profile generally corresponding to the profile of the interface member 138. For example, in the illustrated example, the substrate 144 is a flat and generally rectangular film that generally matches the profile of the illustrated heat exchanging surface 140 of the interface member 138. In other examples, the substrate can have curved, faceted, or other desired profiles to correspond to the interface member 138. In further examples, the substrate 144 can have a profile that corresponds to only a portion of the interface member 138.

The substrate 144 can be substantially flexible to conform to the interface member 138 and have sufficient heat conductivity. As a result, the sensing device 132 does not substantially impede heat transfer between the cooling device 104 and the subject 101. In one example, the substrate 144 can be a thin film constructed from polyimide, polyamide, polycarbonate, or any other suitable material with sufficient heat conductivity. In another example, the substrate 144 can be a thick film attached to a backing material (not shown, e.g., paper, plastic, etc.) with an adhesive. According to aspects of the invention, the substrate 144 can be peeled off the backing material and adhered to the interface member 138 during assembly.

The substrate 144 can also include attachment features for affixing the sensing device 132 to the housing 134. In the illustrated example, the substrate 144 includes clips 152 (identified individually as 152a-d) that correspond to the indentations 142 of the housing 134. Individual clips 152 include protrusions 154 (identified individually as 154a-d) that can fit inside the indentations 142. During assembly, the substrate 144 is snapped onto the housing 134 with the first surface 146a facing the interface member 138. The clips 152 fasten the substrate 144 onto the housing 134 when the protrusions 154 of the clips 152 engage the indentations 142. In other examples, the substrate 144 can be attached to the housing 134 using screws, pins, hinges, or any other suitable attachment mechanism.

The sensing device 132 can also include at least one sensor disposed on the first and/or second surfaces 146a-b of the substrate 144 to measure a parameter of the interface. In the illustrated example, the sensing device 132 includes a first temperature sensor 148 disposed on the first surface 146a and a second temperature sensor 150 disposed on the second surface 146b. The first temperature sensor 148 contacts the interface member 138 after assembly to directly measure temperatures of the heat exchanging surface 140. The second temperature sensor 150 contacts the subject's skin to directly measure skin temperatures during use. In other examples, the sensing device 132 can include other types of sensors or a greater or smaller number of sensors disposed on the substrate 144. For example, the substrate 144 can include only one temperature sensor disposed on the second surface 146b for measuring the skin temperatures or multiple temperature sensors on the second surface 146b for redundancy. Alternatively, or in conjunction with multiple sensors, the substrate can include pressure sensors, transmissivity sensors, bioresistance sensors, ultrasound sensors, optical sensors, infrared sensors, heat flux, any other desired sensors, or any combination thereof.

In the illustrated example, the first and second temperature sensors 148, 150 are configured as thermocouples as described in more detail below with reference to FIGS. 4 and 5. In other examples, the temperature sensors 148, 150 can be configured as Resistive Temperature Detectors (RTD), thermistors, thermopiles, or other types of temperature sensors as described in more detail below with reference to FIG. 6. A thermopile is essentially a series of thermocouples and can be wired to measure temperature difference between two surfaces. In one embodiment, the thermocouples are laminated onto a Kapton backing and measure the temperature across the Kapton backing very accurately, which can then be converted to heat flux. In a further example, the sensing device 132 can include pressure sensors, transmissivity sensors, bioresistance sensors, ultrasound sensors, optical sensors, infrared sensors, heat flux, or any other desired sensors.

A coupling agent may be applied to the subject's skin or to the interface member 138 to provide improved thermal conductivity. The coupling agent may include polypropylene glycol, polyethylene glycol, propylene glycol, and/or glycol. Glycols, glycerols, and other deicing chemicals are efficient freezing-point depressants and act as a solute to lower the freezing point of the coupling agent. Propylene glycol (CH3CHOHCH2OH) is one exemplary component of deicer or non-freezing coupling agents. Other components include polypropylene glycol (PPG), polyethylene glycol (PEG), polyglycols, glycols, ethylene glycol, dimethyl sulfoxide, polyvinyl pyridine, calcium magnesium acetate, sodium acetate, and/or sodium formate. The coupling agent preferably has a freezing point in the range of −40° C. to 0° C., more preferably below −10° C. as further described in U.S. Provisional Application 60/795,799, entitled Coupling Agent For Use With a Cooling Device For Improved Removal of Heat From Subcutaneous Lipid-Rich Cells, filed on Apr. 28, 2006, herein incorporated in its entirety by reference.

In operation, an operator can place the cooling device 104 proximate to the subject's skin to form a heat exchanging interface. In one embodiment, the operator can press the cooling device 104 against the subject's skin. In another embodiment, the operator can clamp a portion of the subject's skin between the cooling device 104 and another device, such as a device similar in function and structure to the cooling device 104. The operator can then exchange heat with the subject's skin using the cooling device 104. In one embodiment, the operator can cool the subject's subcutaneous tissues by circulating a coolant through the heat exchanging member 130 via the fluid lines 108a-b. Heat can then be removed from the subject's skin, past the sensing device 132, to the heat exchanging member 130. By cooling the subcutaneous tissues to a temperature lower than 37° C., preferably between about −20° C. to about 20° C., more preferably between about −20° C. to about 10° C., more preferably between about −15° C. to about 5° C., more preferably between about −10° C. to about 0° C., subcutaneous lipid-rich cells can be selectively affected. The affected cells are resorbed into the subject through natural processes. In any of these embodiments, the operator can monitor and control the heat exchanging process by measuring skin and interface temperatures using the sensing device 132. In one example, the operator can prevent excessively cooling the subject's skin by maintaining the skin and/or interface temperatures at a safe level. In other examples, the skin and/or the interface temperatures can be used as process variables to automatically control the heat exchanging process.

One expected advantage of using the cooling device 104 is the reduced risk of overcooling the subject's skin because the heat transfer interface temperature can be directly measured. As is known, heat conduction through an object creates a temperature gradient along a heat transfer path. For example, the temperature of the subject's dermis can be higher than that of the subject's epidermis during heat conduction. As a result, if the dermis temperature or a temperature internal to the cooling device, is used to control a cooling process, the epidermis temperature may be too high or too low. Consequently, using directly measured interface temperatures (e.g., at the epidermis) can reduce the risk of overheating or overcooling the subject's skin.

The cooling device 104 can have many additional embodiments with different and/or additional features without detracting from the operation of the cooling device 104. For example, the cooling device 104 can be configured to be a handheld device as described in U.S. patent application Ser. No. 11/359,092 entitled Cooling Device For Removing Heat From Subcutaneous Lipid-Rich Cells, the entire disclosure of which is herein incorporated by reference. The heat exchanging member 130 can include thermoelectric heat exchanging members (e.g., Peltier-type elements), cryogenic elements (e.g., liquid Nitrogen evaporator), or other types of suitable heat exchanging elements. For example, the cooling device 104 can be configured as a plurality of thermoelectric heat exchanging members contained on a hinged frame to allow rotation about at least one axis as described in U.S. Patent Application entitled Cooling Device Having a Plurality of Controllable Thermoelectric Cooling Elements to Provide a Predetermined Cooling Profile filed concurrently herewith, application number not yet assigned, the entire disclosure of which is herein incorporated by reference. The sensing device 132 can also be incorporated into a sleeve that can isolate the subject 101 from the heat exchanging member 130 as described below in more detail with reference to FIG. 3.

D. Cooling Devices With Sleeve Sensors

Figure 3:
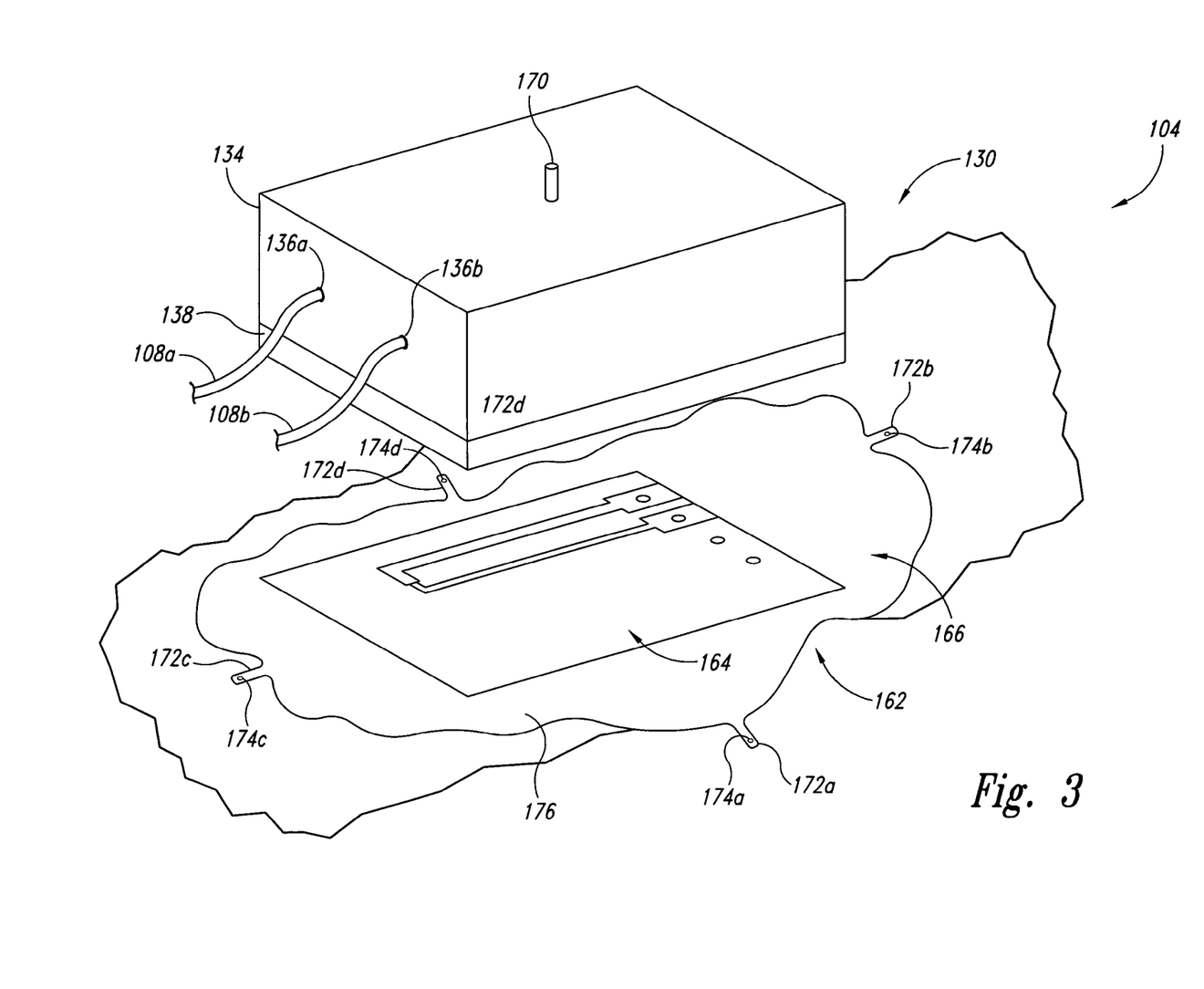
FIG. 3 is a partially exploded isometric view of a cooling device with flexible sensors in accordance with another embodiment of the invention.

FIG. 3 is an alternative example of the cooling device 104 in accordance with one example of the invention for use in the system 100. This alternative example, and those alternative examples and other alternatives described herein, is substantially similar to previously described examples, and common acts and structures are identified by the same reference numbers. Only significant differences in operation and structure are described below. In this example, the cooling device 104 includes a sleeve 162 having a first sleeve portion 164 and a second sleeve portion 166. The first sleeve portion 164 can be generally similar in structure and function to the sensing device 132 of FIG. 2. The second sleeve portion 166 can be an isolation layer extending from the first sleeve portion 164. For example, the second sleeve portion 166 can be constructed from latex, rubber, nylon, Kevlar®, or other substantially impermeable or semipermeable material. The second sleeve portion 166 can prevent any contact between the subject's skin and the heat exchanging member 130. In one example, the sleeve 162 can be reusable. In other examples, the sleeve 162 can be disposable. The sleeve 162 may be provided sterile or non-sterile.

The second sleeve portion 166 can also include attachment features to affix the sleeve 162 to the housing 134. In the illustrated example, the second sleeve portion 166 includes four brackets 172 (identified individually as 172a-d), each located at a corner of the second sleeve portion 166. Individual brackets 172 include an aperture 174 (identified individually as 174a-d) that corresponds to an attachment point 170 of the housing 134. During assembly, the apertures 174 of the brackets 172 can fit over the attachment point 170 such that the second sleeve portion 166 at least partially encloses the heat exchanging member 130. In another example, the second sleeve portion 166 can include brackets that can engage each other. For example, the bracket 172a can include a pin that can engage the aperture 174d of the bracket 172d. During assembly, the second sleeve portion 166 can wrap around the housing 134 and be held in place by engaging the brackets 172 with each other. In a further example, the second sleeve portion 166 can include a flexible member (not shown, e.g., an elastic band) at an outer edge 176 of the second sleeve portion 166 that can hold the sleeve 162 over the housing 134 during assembly. In a further example, the second sleeve portion 166 can include a releasable attachment member (not shown, e.g., Velcro® or snaps) at the outer edge 176 of the second sleeve portion 166 that can hold the sleeve 162 over the housing 134 during assembly. In yet another example, adhesive can hold the second sleeve portion 166 to the housing 134.

In addition to the expected advantages described above, one expected advantage of using the sleeve 162 is the improved sanitation of using the cooling device 104. The sleeve 162 can prevent cross-contamination between the subject's skin and the heat exchanging member 130 because the sleeve 162 is substantially impermeable. Also, operating expense of the cooling device 104 can be reduced because the heat exchanging member 130 does not need to be sanitized after each use.

The sleeve 162 can have many additional embodiments with different and/or additional features without detracting from its operation. For example, the first and second sleeve portions 164, 166 can be constructed from the same material (e.g., polyimide) or different materials. The sleeve 162 can include an adhesive layer (not shown) that binds the sleeve 162 to the housing 134. Alternatively, a coupling gel (not shown) can be applied between the sleeve 162 and the interface member 138.

E. Sensing Devices

Figure 4:
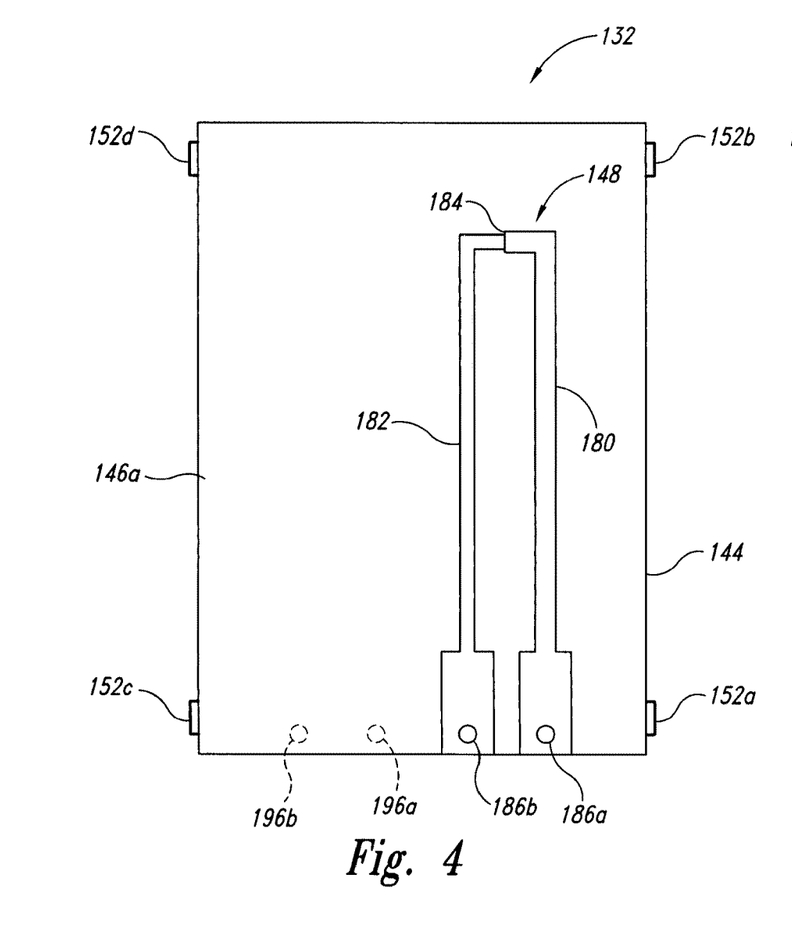
FIG. 4 is a front view of a flexible sensing device in accordance with another embodiment of the invention.
Figure 5:
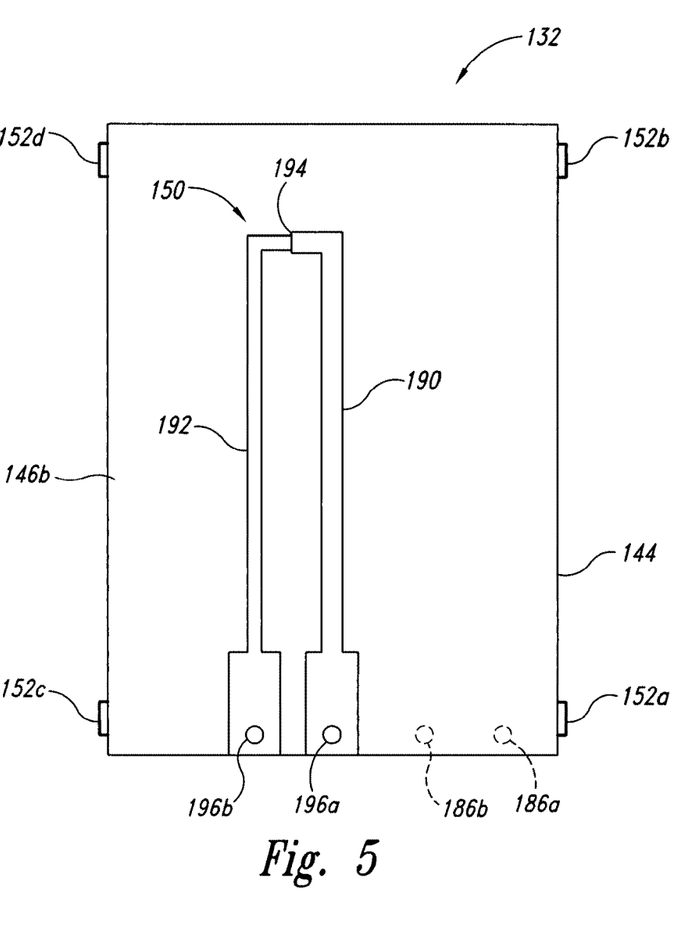
FIG. 5 is a back view of a flexible sensing device in accordance with another embodiment of the invention.

FIG. 4 is a front view and FIG. 5 is a back view of the sensing device 132 illustrating several features in more detail. The first temperature sensor 148 can include a first metal trace 180 and a second metal trace 182 spaced apart from the first metal trace 180. The first metal trace 180 includes a first terminal portion 186a, and the second metal trace 182 includes a second terminal portion 186b. The first and second metal traces 180, 182 join at one end to form a bi-metal junction 184. In the illustrated embodiment, the first and second metal traces 180, 182 are generally parallel to each other. In other examples, the first and second metal traces 180, 182 can be at an angle.

The first and second metal traces 180, 182 can be disposed onto the substrate 144 using techniques including, for example, bonding, laminating, sputtering, etching, printing, or other suitable methods. The first and second metal traces 180, 182 can include iron, constantan, copper, nicrosil, platinum, rhodium, tungsten, or other suitable metals or metal alloys. The first and second metal traces 180, 182 can form thermocouples of the types J, K, T, E, N, R, S, U, B, and other desired types.

In the illustrated example, the second temperature sensor 150 is generally similar in structure and function to the first temperature sensor 148. For example, the second temperature sensor 150 can include metal traces 190, 192 joined at an end to form a bi-metal junction 194 and terminal portions 196a-b. In one embodiment, the first and second temperature sensors 148, 150 can be the same type (e.g., type T). In another embodiment, the first and second temperature sensors 148, 150 can be of different types.

Figure 6:
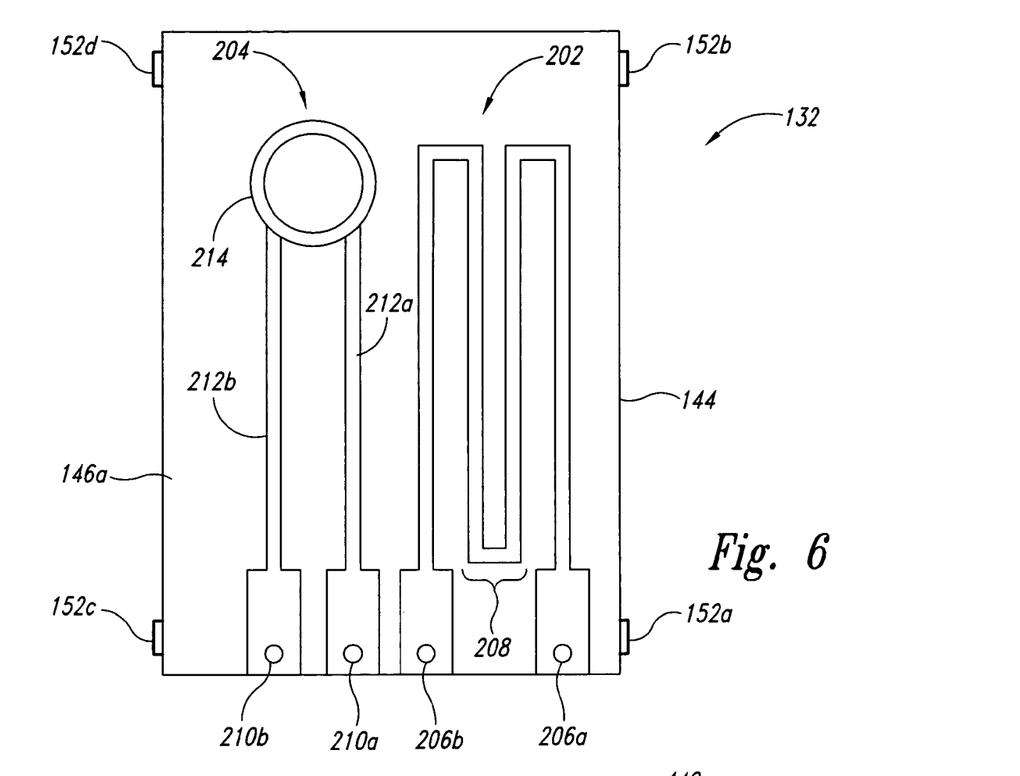
FIG. 6 is a front view of a flexible sensing device in accordance with a further embodiment of the invention.

FIG. 6 is an alternative example of the sensing device 132 in accordance with one example of the invention for use in the system 100. In this example, the sensing device 132 includes an RTD 202 and a pressure sensor 204 disposed on the first surface 146a of the substrate 144. The RTD 202 includes a first RTD terminal 206a, a second RTD terminal 206b, and a resistance portion 208 between the two RTD terminals 206a-b. The resistance portion 208 can be constructed from platinum, gold, silver, copper, nickel or a combination of metals, such as nickel-iron, or any other materials or combinations of materials with sufficient temperature resistance change. A preferred embodiment includes a nickel-iron metal foil. The pressure sensor 204 includes terminals 210a-b, a pressure sensing portion 214, and leads 212a-b connecting the terminals 210a-b to the pressure sensing portion 214. The pressure sensor 204 can be generally similar to a FlexiForce® load sensor (Model No. A201) manufactured by Tekscan, Inc. of South Boston, Massachusetts.

In operation, the RTD 202 senses the interface temperature between the interface member 138 (FIG. 2) and the subject's skin, and the pressure sensor 204 senses the pressure applied to the subject's skin from the cooling device 104 (FIGS. 2 and 3). An operator can then adjust the pressure applied to the subject's skin and/or the heat exchanging rate based on these measurements.

One expected advantage of using the sensing device 132 is the improved uniformity of heat transfer across the heat exchanging interface. If the contact between the interface member 138 and the subject's skin is poor, air gaps in the interface can substantially impede the heat transfer between the cooling device 104 and the subject's skin and cause faulty interface temperature measurements. By using the sensing device 132, the operator can monitor and correct the amount of pressure applied to the subject's skin to ensure good contact at the heat exchanging interface. Consequently, uniformity of the heat transfer across the interface can be improved.

F. Computing System Software Modules

Figure 7:
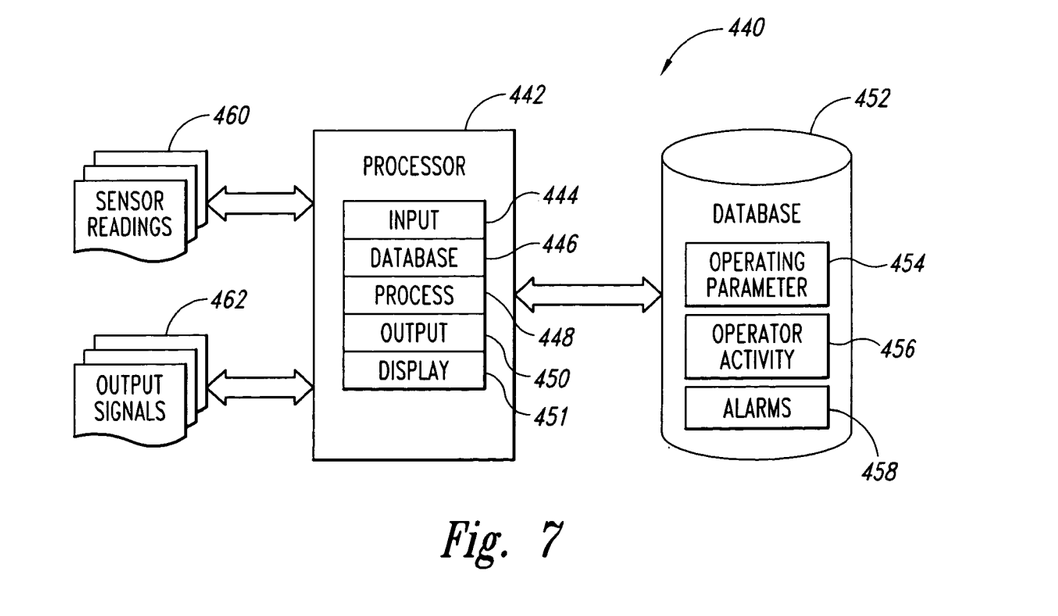
FIG. 7 is a block diagram showing computing system software modules for exchanging heat with a subject in accordance with an embodiment of the invention.

FIG. 7 illustrates a functional block diagram showing exemplary software modules 440 suitable for use in the processing unit 114 (FIG. 1). Each component can be a computer program, procedure, or process written as source code in a conventional programming language, such as the C++ programming language, and can be presented for execution by the CPU of a processor 442. The various implementations of the source code and object and byte codes can be stored on a computer-readable storage medium or embodied on a transmission medium in a carrier wave. The modules of the processor 442 can include an input module 444, a database module 446, a process module 448, an output module 450, and optionally, a display module 451. In another embodiment, the software modules 440 can be presented for execution by the CPU of a network server in a distributed computing scheme.

In operation, the input module 444 accepts an operator input, such as process setpoint and control selections, and communicates the accepted information or selections to other components for further processing. The database module 446 organizes records, including operating parameter 454, operator activity 456, alarm 458, and facilitates storing and retrieving of these records to and from a database 452. Any type of database organization can be utilized, including a flat file system, hierarchical database, relational database, or distributed database, such as provided by Oracle Corporation, Redwood Shores, California.

The process module 448 generates control variables based on sensor readings 460 obtained from the sensing device 132 (FIG. 2), and the output module 450 generates output signals 462 based on the control variables. For example, the output module 450 can convert the generated control variables from the process module 448 into 4-20 mA output signals 462 suitable for a direct current voltage modulator. The processor 442 optionally can include the display module 451 for displaying, printing, or downloading the sensor readings 460 and output signals 462 via devices such as the output device 120 (not shown). A suitable display module 451 can be a video driver that enables the processor 442 to display the sensor readings 460 on the output device 120.

Throughout the description and the claims, the words "comprise," "comprising," and the like, unless the context clearly requires otherwise, are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can be combined to provide further embodiments.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

We claim:

1. A cooling system comprising:
   a cooling device configured to non-invasively remove heat from subcutaneous lipid-rich cells of a subject to substantially affect the lipid-rich cells while non-lipid-rich cells in the subject's epidermis are not substantially affected, the cooling device including
      a first cooling element having a first cooling surface and a first sensing device overlaying the first cooling surface, and
      a second cooling element hingedly connected to the first cooling element, the second cooling element having a second cooling surface and a second sensing device overlaying the second cooling surface; and
   wherein the cooling device is configured to be in communication with a processing unit programmed to
      control operation of the first cooling element based on first sensor readings from the first sensing device, and control operation of the second cooling element based on second sensor readings from the second sensing device.

2. The cooling system of claim 1, wherein the processing unit is configured for independently controlling operation of the first and second cooling elements.

3. The cooling system of claim 1, further comprising a hinged segmented frame hingedly interconnecting the first and second cooling elements.

4. The cooling system of claim 1, wherein
   the first cooling element includes a thermoelectric element, and
   the first sensing device includes at least one sensor and a substrate overlaying the at least one sensor, wherein the at least one sensor is positioned between the thermoelectric element and at least a portion of the substrate.

5. The cooling system of claim 1, wherein the processing unit is programmed to command the cooling device based on at least one of (a) skin temperatures or (b) skin-cooling device interface temperatures.

\* \* \* \* \*